US009872646B2

(12) United States Patent
Harttig (10) Patent No.: US 9,872,646 B2
(45) Date of Patent: Jan. 23, 2018

(54) METHOD FOR PRODUCING A MEMBRANE RING OR TEST STRIP RING AND RING MAGAZINE

(71) Applicant: Roche Diabetes Care, Inc., Indianapolis, IN (US)

(72) Inventor: Herbert Harttig, Neustadt (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/596,915

(22) Filed: Jan. 14, 2015

(65) Prior Publication Data
US 2015/0141870 A1    May 21, 2015

Related U.S. Application Data

(63) Continuation of application No. 13/647,781, filed on Oct. 9, 2012, now abandoned, which is a continuation
(Continued)

(30) Foreign Application Priority Data

May 5, 2010    (EP) ..................... 10162064

(51) Int. Cl.
*A61B 5/00* (2006.01)
*A61B 5/15* (2006.01)
(Continued)

(52) U.S. Cl.
CPC .... *A61B 5/150358* (2013.01); *A61B 5/14532* (2013.01); *A61B 5/151* (2013.01);
(Continued)

(58) Field of Classification Search
CPC ................... A61B 5/150274; A61B 5/150282
(Continued)

(56) References Cited

U.S. PATENT DOCUMENTS 2,046,988 A    7/1936    Winter
4,260,047 A    4/1981    Nels
(Continued)

FOREIGN PATENT DOCUMENTS

CN    1662174 A    8/2005
CN    1735370 A    2/2006
(Continued)

OTHER PUBLICATIONS

International Preliminary Report on Patentability, International Application No. PCT/EP2011/057193, 5 pages.
Machine Translation of Abstract of SU 776630 B.

*Primary Examiner* — Daniel Cerioni
(74) *Attorney, Agent, or Firm* — Quarles & Brady LLP (57) ABSTRACT

A method for producing a membrane ring or test strip ring for a diagnostic test device includes an elongate strip that is divided into segments by cuts running transversely to the longitudinal direction of the strip, where the cuts are made only as far as a residual width of the strip so that a material bridge remains intact between the segments adjacent to the cuts (24). The strip is closed by bringing its ends together to form a ring where the cut edges of the cuts running towards the material bridges each enclose an acute angle (α). The ring is inserted into a support structure as a membrane ring or test strip ring for the test device.

44 Claims, 5 Drawing Sheets

Related U.S. Application Data of application No. PCT/EP2011/057193, filed on May 5, 2011.

(51) Int. Cl.
*A61B 5/145* (2006.01)
*A61B 5/151* (2006.01)
*B01L 3/00* (2006.01)
*G01N 33/487* (2006.01)
*A61B 5/157* (2006.01)

(52) U.S. Cl.
CPC ........ *A61B 5/157* (2013.01); *A61B 5/150022* (2013.01); *A61B 5/15148* (2013.01); *A61B 5/15151* (2013.01); *A61B 5/15161* (2013.01); *A61B 5/150274* (2013.01); *B01L 3/5023* (2013.01); *G01N 33/4875* (2013.01); *A61B 5/15176* (2013.01); *A61B 2562/0295* (2013.01); *B01L 2200/04* (2013.01); *B01L 2300/0663* (2013.01); *B01L 2300/0803* (2013.01); *B01L 2300/0825* (2013.01); *Y10T 29/49826* (2015.01)

(58) Field of Classification Search
USPC ........................................................ 600/583
See application file for complete search history.

(56) References Cited

U.S. PATENT DOCUMENTS

| | | |
|---|---|---|
| 4,726,455 A | 2/1988 | East |
| 4,878,282 A | 11/1989 | Bauer |
| 5,120,296 A | 6/1992 | Yamaguchi et al. |
| 5,800,779 A | 9/1998 | Johnson |
| 5,897,737 A | 4/1999 | Quigley |
| 6,203,649 B1 | 3/2001 | Kremsmair et al. |
| 7,771,367 B2 | 8/2010 | Haar et al. |
| 7,883,494 B2 | 2/2011 | Martin |
| 8,196,500 B2 | 6/2012 | Mansfield et al. |
| 2004/0092995 A1 | 5/2004 | Boecker et al. |
| 2004/0230216 A1 | 11/2004 | Levaughn et al. |
| 2005/0071979 A1 | 4/2005 | Guthrie et al. |
| 2005/0072649 A1 | 4/2005 | Guthrie et al. |
| 2006/0157362 A1 | 7/2006 | Schraga |
| 2007/0088377 A1 | 4/2007 | Levaughn et al. |
| 2007/0199794 A1 | 8/2007 | Miyazaki et al. |
| 2009/0264720 A1 | 10/2009 | Torjman et al. |
| 2010/0092338 A1 | 4/2010 | List et al. |

FOREIGN PATENT DOCUMENTS

| | | |
|---|---|---|
| EP | 0305582 B1 | 6/1991 |
| EP | 0756101 A1 | 1/1997 |
| SU | 776630 B | 11/1980 |
| WO | 2009/037192 A1 | 3/2009 |

METHOD FOR PRODUCING A MEMBRANE RING OR TEST STRIP RING AND RING MAGAZINE

CROSS-REFERENCE TO RELATED APPLICATIONS

This patent application is a continuation of U.S. patent application Ser. No. 13/647,781 (filed 9 Oct. 2012), which is a continuation of Int'l Patent Application No. PCT/EP2011/057193 (filed 5 May 2011), which claims priority to European Patent Application No. 10162064.9 (filed 5 May 2010). Each patent application is incorporated herein by reference as if set forth in its entirety.

FIELD OF THE INVENTION

The invention concerns a method for producing a membrane ring or test strip ring for a diagnostic test device for examining body fluids. The invention additionally concerns a ring magazine for a diagnostic test device.

BACKGROUND

The use of microfiltration membranes in the form of strips or discs is well known in the field of medical diagnostics. Also, the use of disc-shaped magazines in hand-held devices for blood sugar measurements is, for example, known from WO2009/037192. A disadvantage of directly cutting flat rings of material is the loss of material, which is very pronounced especially in the case of narrow rings. Hence, in the case of a ring of 49 mm outer diameter and 39 mm inner diameter, one only uses 28.8% of a quadratic initial area from which the ring is cut. If rings are cut out of an initial area in the densest possible arrangement, then theoretically 33.2% can be utilized at most, but in practice less. With the high costs of membranes, the yield of utilizable area plays an important economic role above all for mass-produced products. Moreover, the handling of individual membrane areas is time consuming and mechanically demanding and prone to errors Therefore further advancements are required in this technological area to further improve the processes and devices known in the prior art and to optimize the use of material and handling of consumables in the field of diagnostic applications.

SUMMARY

There is disclosed herein providing an analytical material segment in each case for a plurality of single tests in a circular arrangement especially as a magazine. Accordingly it is proposed that an elongate strip is provided by cutting a flat or tape-shaped starting material is divided into segments by cuts running transversely (i.e. at right angles or diagonally) to the longitudinal direction of the strip. The cuts are made only as far as a residual width that may vary of the strip so that a material bridge remains intact between the segments adjacent to the cuts. The strip is closed by bringing its ends together to form a ring, where the cut edges of each of the cuts running towards the material bridges enclose an acute angle. The ring is inserted into a support structure as a membrane ring or test strip ring for the test device. In this manner it is possible to avoid directly punching out a material ring and to minimize the amount of material that has to be discarded during the production process. In addition, automation can be simplified by a linear pre-production, for example, from roll to roll. At the same time, the segmentation particularly simplifies a division into single tests.

According to one embodiment the strip should be cut to a residual width of 0.1 to 1.0 mm that remains as a material bridge in order to ensure sufficient flexibility. A uniform residual width can be selected.

Another embodiment provides that the strip is uniformly cut into from one of its longitudinal edges so that the material bridges remain at the other longitudinal edge. If the material bridges lie at the outer edge of the ring that is subsequently formed, the overlap of the segments is at a maximum, whereas in the case of material bridges at the inner edge no overlap occurs.

According to a further embodiment, the strip is cut two-sided in each case on one line from both of its longitudinal edges while retaining a material bridge.

The cuts can be made with a cutting or punching tool or by laser cutting. The cut with a laser compresses the cut edge and thus stabilizes the material bridge. Hence, a laser cut is preferred but not required.

As far as the manufacturing process is concerned, in one embodiment, when the cut strip, it is twisted lengthwise before ring formation so that the segments are tilted at a continuously increasing angle relative to a tilt axis running through the material bridges. This enables a subsequent ring formation without the cut edges getting caught up in one another.

In another embodiment, the segments are successively put down on a flat ring surface during the ring formation and in doing so are brought from a tilted position into a mutually overlapping position. In the aforementioned step, the ring can be formed in such a manner that the material bridges span a circle, wherein the ends of the strip make contact on the circle.

Another embodiment can be achieved in that the segments are put down overlapping in pairs during ring formation, wherein the overlaps bounded by the cut edges of the cuts run from the inner side of the ring to the respective material bridge.

In order to stabilize the ring that has formed, neighbouring segments can be joined to one another in an overlapping manner under the action of heat and/or pressure and in particular welded or glued. In one embodiment, when mutually joining the segments, the ring is at the same time attached to the support structure, such as a magazine.

Another embodiment envisages a starting material that is formed by a foil coated with a reactive test chemistry or by a membrane that is at least partially permeable to the body fluid. A membrane ring can be mounted on a test strip ring with pairwise contact of the double-sided segments. It is also conceivable that individual test fields are applied to the segments of one membrane ring or vice versa.

In the context of diagnostic applications, the segments can be provided or arranged as disposables in a ring magazine, and can be separated in chambers each for a single test. Such chambers can be each furnished with one lancing or needle element for collecting body fluid.

The closed ring can be inserted into a disc-shaped housing as a support structure so that each of the segments are allocated to one chamber of the housing.

A further embodiment provides that a cut is made in the strip at right angles from a longitudinal edge, wherein the cut edges of the cuts formed in this manner in each case run in pairs parallel to a common cut line.

In order to realize a test strip ring, a foil coated with a reactive test chemistry for an analyte in the body fluid is used as a starting material. A filter membrane can be used as a starting material for a membrane ring for the selective separation of components of the body fluid.

According to another aspect, a ring magazine is disclosed for a diagnostic test device, in particular for examining body fluids, comprising a support structure and a membrane ring or test strip ring inserted therein that has been produced according to the method discussed above, wherein the ring that is inserted as a closed circumferential structure is formed from a strip material segmented by cuts and the segments joined by material bridges form a filter or a detection element for a single test in each case. Thus, such a membrane ring or test strip ring has a strip which is subdivided into segments by edge cuts transverse to the longitudinal direction, wherein the cuts run only as far as an optionally varying residual width of the strip so that a material bridge remains intact between the segments adjacent to the cuts and wherein the strip is closed to form a ring so that the cut edges of the cuts running towards the material bridges each enclose an acute angle.

The support structure of such a ring magazine can have openings or windows to transfer body fluid, wherein the openings are each covered by a segment of the membrane ring or test strip ring. The support structure can have test chambers arranged in a ring shape in a disc-shaped housing, and in one embodiment each test chamber contains a lancing element and each of which is allocated to a segment of the membrane ring or test strip ring for carrying out a single test. In this connection the segments can each have a free application site for taking up body fluid.

Another aspect concerns a diagnostic test device which is configured for the successive segment by segment processing of a ring magazine as discussed above. In particular the replaceable ring magazine can be mounted so that it can be rotated in such an instrument or can be rotated by a rotary drive in order to provide the individual segments at a defined application site.

BRIEF DESCRIPTION OF THE FIGURES

The invention is further elucidated in the following on the basis of an embodiment example shown schematically in the drawing.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated herein.

Figure 1:
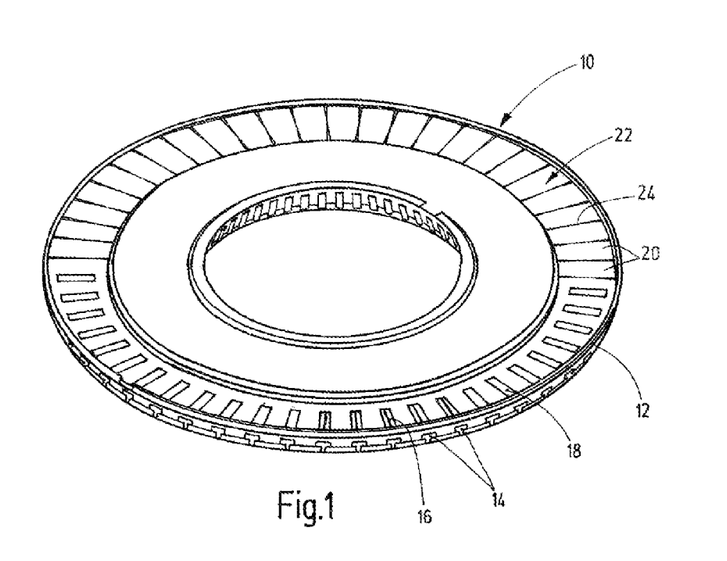
FIG. 1 shows a ring magazine for a diagnostic test device with a test strip ring only half of which is shown in a perspective view.

The ring magazine 10 shown in FIG. 1 can be inserted as a consumable into a mobile analyzer for blood sugar analytes (not shown). For this purpose it comprises a disc-shaped housing 12 as a support structure which contains a plurality of chambers 14 arranged in a circle for receiving lancing elements 16 that can be pushed out radially, wherein an opening 18 is provided on the housing cover over each of the chambers 12 through which blood obtained from a body puncture can be transferred for a photometric glucose detection on a segment 20 of a test strip ring 22. The test strip ring can be provided with a dry chemistry reagent layer which takes up the applied body fluid and reacts with an analyte contained therein such as glucose. It is also conceivable that a membrane ring is mounted as a filter for transferring blood between the lancing elements 16 and a test ring.

In order to produce such a test strip or membrane ring 22 in a manner that saves as much material as possible, a ring manufactured from a strip material segmented by cuts 24 is provided as further elucidated in the following. This avoids having to directly punch out a flat material ring and the amount of material that has to be discarded during the production process is minimized.

Figure 2:
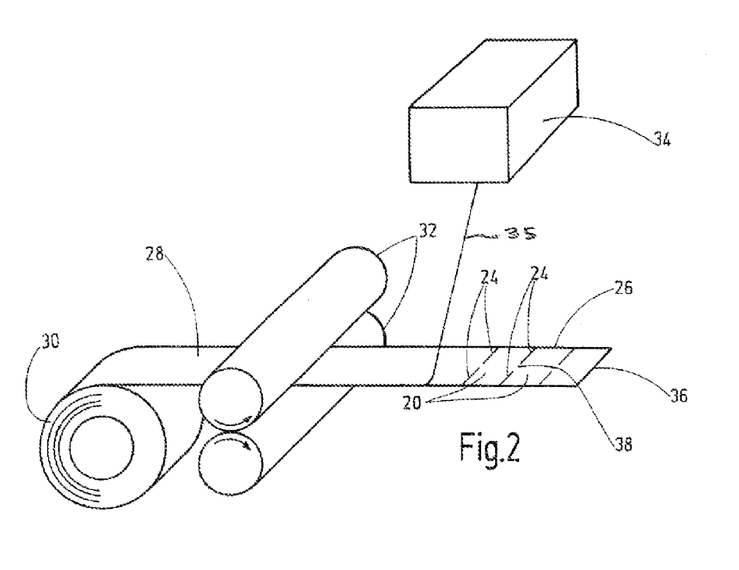
FIG. 2 shows a diagrammatic representation of a device for prefabricating a cut test strip.

FIG. 2 illustrates the pre-production of a cut tape strip 26. In this process a tape 28 as the starting material is pulled from a supply spool 30 and guided over transport rollers 32. A laser 34 as a cutting device enables the strip 26 to be cut to length at the strip ends by means of a laser beam 35 and the introduction of the cuts 24 to form the segments 20 in the tape material. Alternatively it is also conceivable to firstly cut strips from a starting material having a large area and to then provide them with transverse cuts.

Figure 3:
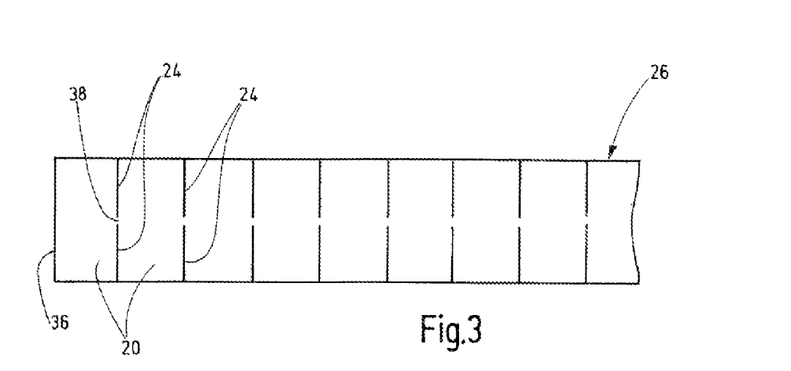
FIGS. 3-5 show various stages of a material-saving formation of the test strip ring from the prefabricated test strip in a broken top-view.

As shown in FIG. 3 the strip 26 in the embodiment example shown is cut into on both sides in each case on a transverse line at right angles to the longitudinal edges so that a central material bridge 38 remains intact between adjacent segments 20. It is also possible that the strip is cut uniformly at right angles from a longitudinal or side edge so that the material bridges are then located at the opposite ends of the other longitudinal edge. The cuts 24 are advantageously at the same distance from one another when viewed in the longitudinal direction of the strip 26 in order to obtain congruent segments 20.

For example, a tape material of 90 µm thickness can be cut into a strip having a length of 140 mm and a width of 5 mm, while the cuts are at a longitudinal distance of 2.8 mm from one another and run transversely by 2.4 mm in each case from both longitudinal edges so that a material bridge of 0.2 mm remains.

Figure 4:
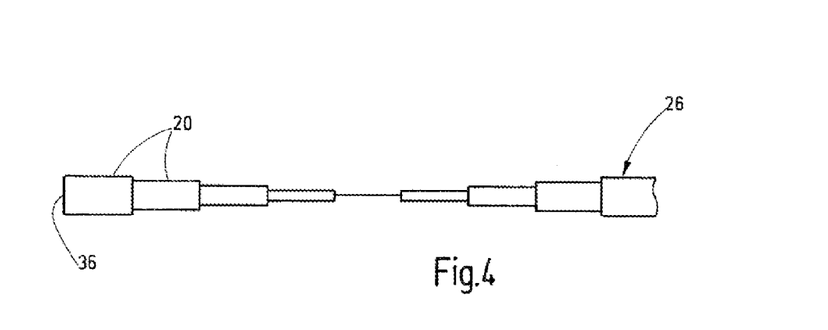

As shown in FIG. 4 the cut strip 26 is twisted in its longitudinal direction before ring formation so that the segments 20 are tilted and rotated at a continuously increasing angle relative to a longitudinal axis running through the material bridges 38 and correspondingly appear to be of different widths in the top-view. This measure enables a collision-free ring formation with mutual overlap of the segments 20.

Figure 5:
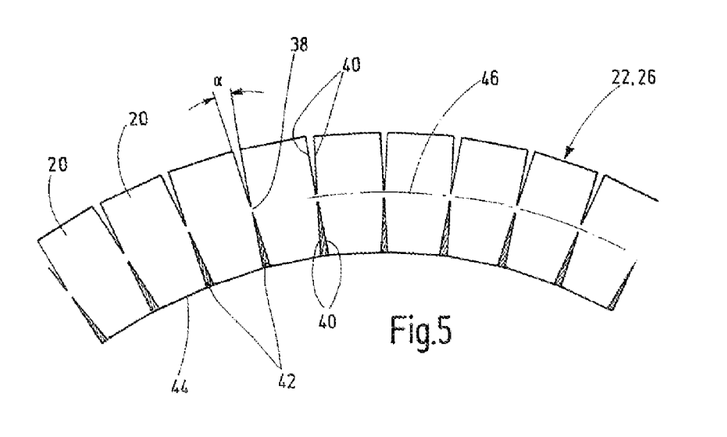

FIG. 5 illustrates the formation of the ring 22 from the prefabricated strip 26 according to FIGS. 3 and 4. In this process the segments 20 are successively placed down on a flat ring surface and expediently directly on the housing cover. As they are placed down, the tilted position of the segments 20 is returned into a mutual overlap position. The overlapping areas 42 bordered by the opposing cut edges 40 of the cuts 24 then run from the inner side of the ring 44 to the respective material bridge 38 while the radial outer cut edges 40 also diverge starting from the respective material bridge 38 under an acute angle α. In the ring 26 formed in this manner the material bridges span a circle 46 where the two ends 36 of the strip 26 make contact on the line of the circle.

The segments 20 are expediently welded together in the overlapping areas 42 by the action of heat and pressure for example by means of an appropriately structured heated stamp or by means of a transparent stamp and laser light. In this process it is possible at the same time to achieve an integral attachment on the housing cover.

While the invention has been illustrated and described in detail in the drawings and foregoing description, the same is to be considered as illustrative and not restrictive in character, it being understood that only certain exemplary embodiments have been shown and described and that all changes and modifications that come within the spirit of the inventions are desired to be protected. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method for producing a diagnostic test device for examining body fluids, the method comprising the steps of:
    a) forming a starting material from one of a foil coated with a reactive test chemistry and a membrane that is at least partially permeable to body fluid to filter the body fluid passing through the membrane;
    b) cutting an elongate strip of the starting material into segments, such that the elongate strip includes two ends and the segments are divided by cuts running transversely to a longitudinal direction of the elongate strip, wherein the cuts are made to maintain a material bridge between the segments adjacent to the cuts;
    c) closing the elongate strip by bringing the ends together to form a ring, wherein cut edges of each of the cuts running towards the material bridges diverge from adjacent cuts and enclose an acute angle;
    d) providing a support structure for the diagnostic test device, the support structure having a disc-shaped housing that includes a plurality of chambers;
    e) inserting the ring into the disc-shaped housing so that each of the segments is allocated to a respective one of the chambers of the housing; and
    wherein the elongate strip is cut to a residual width of 0.1 to 1.0 mm that remains as the material bridge.

2. The method according to claim 1, wherein the elongate strip is uniformly cut into from a longitudinal edge of the elongate strip such that the material bridges remain at an opposite longitudinal edge of the elongate strip.

3. The method according to claim 1, wherein the elongate strip is cut from opposing longitudinal edges of the elongate strip while retaining the material bridge between cuts extending from the opposing longitudinal edges.

4. The method according to claim 1, wherein the cuts are made using a cutting or punching tool or by laser cutting.

5. The method according to claim 1, further comprising twisting the cut strip lengthwise before closing the elongate strip to form the ring so that the segments are tilted at a continuously increasing angle relative to a tilt axis running through the material bridges.

6. The method according to claim 5, further comprising successively placing the segments down on a flat ring surface to bring the segments from a tilted position into a mutually overlapping position.

7. The method according to claim 1, wherein the ring is configured so that the material bridges span a circle wherein the ends of the elongate strip make contact on the circle.

8. The method according to claim 1, wherein adjacent ones of the segments are placed to form overlaps during ring formation, wherein the overlaps extend from an inner side of the ring to the respective material bridge.

9. The method according to claim 8, wherein adjacent segments are joined to one another at the overlap.

10. The method according to claim 9, wherein the adjacent segments are joined at the overlap under the action of heat.

11. The method according to claim 10, wherein the adjacent segments are welded at the overlap.

12. The method according to claim 9, wherein the adjacent segments are joined at the overlap under the action of pressure.

13. The method according to claim 12, wherein the adjacent segments are glued at the overlap.

14. The method according to claim 9, wherein the segments are mutually joined while the ring is at the same time attached to the support structure.

15. The method according to claim 1, wherein the segments are arranged as disposables in a ring magazine and each segment is configured to provide a single test for examining the body fluid.

16. The method according to claim 1, wherein the cuts are made in the elongate strip at right angles from a longitudinal edge of the elongate strip, wherein the cut edges of the cuts run in pairs parallel to a common cut line.

17. The method according to claim 1, wherein the reactive test chemistry is for an analyte in the body fluid.

18. The method according to claim 1, wherein the elongate strip is provided from a flat starting material.

19. The method according to claim 1, wherein the elongate strip is provided from a tape-shaped starting material.

20. A method for producing a diagnostic test device for examining body fluids, the method comprising the steps of:
    a) forming a starting material from one of a foil coated with a reactive test chemistry and a membrane that is at least partially permeable to body fluid to filter the body fluid passing through the membrane;
    b) cutting an elongate strip of the starting material into segments, such that the elongate strip includes two ends and the segments are divided by cuts running transversely to a longitudinal direction of the elongate strip, wherein the cuts are made to maintain a material bridge between the segments adjacent to the cuts and wherein the elongate strip is cut to maintain a residual width of between 2% and 20% of a width of the elongate strip as the material bridge;
    c) closing the elongate strip by bringing the ends together to form a ring, wherein cut edges of each of the cuts running towards the material bridges diverge from adjacent cuts and enclose an acute angle;
    d) providing a support structure for the diagnostic test device, the support structure having a disc-shaped housing that includes a plurality of chambers; and
    e) inserting the ring into the disc-shaped housing so that each of the segments is allocated to a respective one of the chambers of the housing.

21. A ring magazine for a diagnostic test device for examining body fluids, comprising:
    a support structure and a ring inserted in the support structure;
    wherein the ring includes an elongate strip of starting material cut into segments divided by cuts running transversely to a longitudinal direction of the elongate strip;

wherein the cuts are made to maintain a material bridge between the segments adjacent to the cuts and the elongate strip is closed by bringing opposite ends of the elongate strip together to form the ring;

wherein the cuts running transversely to a longitudinal direction of the elongate strip extend through between 80% to 98% of the elongate strip to maintain the material bridge;

wherein cut edges of each of the cuts running towards the material bridges diverge from adjacent cuts and enclose an acute angle; and wherein the support structure includes a plurality of test chambers and each of the segments is allocated to a respective one of the test chambers of the support structure to provide a filter or a detection element configured for a single test for examining the body fluid.

22. The ring magazine according to claim 21, wherein the support structure has a plurality of openings for the transfer of body fluid and the openings are each covered by a respective one of the segments of the ring.

23. The ring magazine according to claim 21, wherein the support structure has a disc-shaped housing including the test chambers arranged in a ring shape.

24. The ring magazine according to claim 21, wherein the segments each have an application site for taking up body fluid.

25. The ring magazine according to claim 21, wherein the ring is placed as a filter in front of a ring-shaped detection element.

26. The ring magazine according to claim 21, wherein the support structure is configured for insertion into a housing of a diagnostic test device.

27. The method according to claim 20, wherein the elongate strip is uniformly cut into from a longitudinal edge of the elongate strip such that the material bridges remain at an opposite longitudinal edge of the elongate strip.

28. The method according to claim 20, wherein the elongate strip is cut from opposing longitudinal edges of the elongate strip while retaining the material bridge between cuts extending from the opposing longitudinal edges.

29. The method according to claim 20, wherein the cuts are made using a cutting or punching tool or by laser cutting.

30. The method according to claim 20, further comprising twisting the cut strip lengthwise before closing the elongate strip to form the ring so that the segments are tilted at a continuously increasing angle relative to a tilt axis running through the material bridges.

31. The method according to claim 30, further comprising successively placing the segments down on a flat ring surface to bring the segments from a tilted position into a mutually overlapping position.

32. The method according to claim 20, wherein the ring is configured so that the material bridges span a circle wherein the ends of the elongate strip make contact on the circle.

33. The method according to claim 20, wherein adjacent ones of the segments are placed to form overlaps during ring formation, wherein the overlaps extend from an inner side of the ring to the respective material bridge.

34. The method according to claim 33, wherein adjacent segments are joined to one another at the overlap.

35. The method according to claim 34, wherein the adjacent segments are joined at the overlap under the action of heat.

36. The method according to claim 35, wherein the adjacent segments are welded at the overlap.

37. The method according to claim 34, wherein the adjacent segments are joined at the overlap under the action of pressure.

38. The method according to claim 37, wherein the adjacent segments are glued at the overlap.

39. The method according to claim 34, wherein the segments are mutually joined while the ring is at the same time attached to the support structure.

40. The method according to claim 20, wherein the segments are arranged as disposables in a ring magazine and each segment is configured to provide a single test for examining the body fluid.

41. The method according to claim 20, wherein the cuts are made in the elongate strip at right angles from a longitudinal edge of the elongate strip, wherein the cut edges of the cuts run in pairs parallel to a common cut line.

42. The method according to claim 20, wherein the reactive test chemistry is for an analyte in the body fluid.

43. The method according to claim 20, wherein the elongate strip is provided from a flat starting material.

44. The method according to claim 20, wherein the elongate strip is provided from a tape-shaped starting material.

* * * * *